United States Patent
Finlayson et al.

(10) Patent No.: US 10,116,133 B2
(45) Date of Patent: Oct. 30, 2018

(54) ELECTRICAL MEANS TO LIMIT CURRENT IN BATTERY OPERATED PATIENT-CONNECTED MEDICAL DEVICES

(75) Inventors: Dana Charles Finlayson, Reading, MA (US); Andreas Richmond Knapp, Groton, MA (US); Francis Kusti Makie, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1208 days.

(21) Appl. No.: 13/984,857

(22) PCT Filed: Feb. 7, 2012

(86) PCT No.: PCT/IB2012/050546
§ 371 (c)(1),
(2), (4) Date: Aug. 12, 2013

(87) PCT Pub. No.: WO2012/110913
PCT Pub. Date: Aug. 23, 2012

(65) Prior Publication Data
US 2013/0313917 A1 Nov. 28, 2013

Related U.S. Application Data

(60) Provisional application No. 61/442,312, filed on Feb. 14, 2011.

(51) Int. Cl.
*H01H 35/00* (2006.01)
*H02H 11/00* (2006.01)
(Continued)

(52) U.S. Cl.
CPC ......... *H02H 11/00* (2013.01); *A61B 5/04288* (2013.01); *A61N 1/3931* (2013.01);
(Continued)

(58) Field of Classification Search
CPC .... A61B 1/041; A61B 1/00158; A61M 5/142; Y02T 10/7005; Y02T 10/7077; B60L 11/14; B60L 11/123
See application file for complete search history.

(56) References Cited

U.S. PATENT DOCUMENTS 4,423,456 A 12/1983 Zaidenweber
4,578,628 A 3/1986 Siwiak
(Continued)

FOREIGN PATENT DOCUMENTS

DE 202008017194 8/2009
JP 02281553 A 11/1990
(Continued)

*Primary Examiner* — Sibin Chen

(57) ABSTRACT

A system (116, 120) for electrically limiting leakage current in a patient-connected medical device (100). The system (116, 120) includes a first set (116) of one or more switching devices (118) that selectively connect a first power output (124) of a battery compartment (110) of the patient-connected medical device (100) with a first power input (126) of electronic components (102) of the patient-connected medical device (100) based on a first polarity of input voltage from the battery compartment (110). The system (116, 120) further includes a second set (120) of one or more switching devices (122) that selectively connect a second power output (128) of the battery compartment (110) of the patient-connected medical device (100) with a second power input (130) of the electronic components (102) based on a second polarity of the input voltage, wherein the first polarity is opposite the second polarity.

20 Claims, 3 Drawing Sheets

(51) Int. Cl.
  *A61B 5/0428*  (2006.01)
  *A61N 1/39*  (2006.01)
  *H02H 5/12*  (2006.01)
  *H01M 2/10*  (2006.01)
  *H01H 11/00*  (2006.01)

(52) U.S. Cl.
  CPC .......... *H01H 11/00* (2013.01); *H01M 2/1022* (2013.01); *H02H 5/12* (2013.01); *A61B 2560/0204* (2013.01); *Y10T 29/49105* (2015.01); *Y10T 307/858* (2015.04)

(56) References Cited

U.S. PATENT DOCUMENTS

| | | | |
|---|---|---|---|
| 5,287,013 A | 2/1994 | Adair | |
| 2003/0174449 A1 | 9/2003 | Yamamoto | |
| 2005/0118862 A1* | 6/2005 | Mehki | H01R 11/282 439/502 |
| 2005/0134216 A1 | 6/2005 | Tokano | |
| 2008/0209965 A1* | 9/2008 | Maack | G06F 21/554 70/262 |
| 2009/0079434 A1* | 3/2009 | Osawa | G01R 31/007 324/434 |
| 2009/0130541 A1* | 5/2009 | Emori | H02J 7/0019 429/61 |

FOREIGN PATENT DOCUMENTS

| | | |
|---|---|---|
| JP | 04284349 A | 10/1992 |
| JP | 10097876 A | 4/1998 |
| JP | 2000323108 A | 11/2000 |

\* cited by examiner

ELECTRICAL MEANS TO LIMIT CURRENT IN BATTERY OPERATED PATIENT-CONNECTED MEDICAL DEVICES

CROSS REFERENCE TO RELATED APPLICATIONS

This application is a national filing of PCT application Serial No. PCT/IB2012/050546, filed Feb. 7, 2012, published as WO 2012/110913 A2 on Aug. 23, 2012, which claims the benefit of U.S. provisional application Ser. No. 61/442,312 filed Feb. 14, 2011, which is incorporated herein by reference.

The present application relates generally to battery operated patient-connected medical devices. It finds particular application in conjunction with limiting leakage current for patient-connected medical devices, and will be described with particular reference thereto. However, it is to be understood that it also finds application in other usage scenarios, and is not necessarily limited to the aforementioned application.

Patient-connected medical devices must generally meet safety standards limiting leakage current on patients. For example, medical markets throughout the world use International Standard IEC 60601-1, Second Edition, 1988-12 as a basis for approval of medical products. IEC 60601-1 requires that any exposed live component of a medical device be isolated from a patient connection and specifies the level of isolation required. 10 microamps, for example, is the limit on patient leakage current for cardiac function (CF) rated devices. Limits on leakage current are important for, inter alia, patients with internal connections where skin impedance does not limit leakage current and patients with sensitive medical implants, which could be life sustaining.

When changing batteries in a medical device with a power source including one or more batteries, battery connection terminals for batteries not yet installed may be accessible and live due to a series connection of batteries already installed. If a patient attached to the medical device were to come in contact with one of these battery connection terminals, the resultant leakage current could exceed safety limits. The only limitations on current flow would be the source impedance of the batteries, the patient impedance, indirect path impedance, and the patient connection impedance. Contact with a live battery connection terminal could occur from the patient touching the battery connection terminal directly or indirectly through a care-giver who is changing the batteries.

To limit patient leakage current, mechanical means inhibiting access to the battery connection terminals could be employed. However, mechanical means are cumbersome for users and expensive to manufacture. Another way to limit patient leakage current would be to increase the patient connection impedance. However some patient parameter measurements, such as respiration, necessarily require low input impedance. Yet another potential way to limit patient leakage current would be to isolate patient inputs by galvanic means, such as transformers and/or optical isolators. However, these approaches are expensive, power consuming, and require valuable space. They defeat a major advantage of a small, light-weight, battery-operated medical device.

The present application provides new and improved systems and methods employing electrical means to overcome the above-referenced problems and others.

In accordance with another aspect, a system for electrically limiting leakage current in a patient-connected medical device is provided. The system includes a first set of one or more switching devices that selectively connect a first power output of a battery compartment of the patient-connected medical device with a first power input of electronic components of the patient-connected medical device based on a first polarity of input voltage from the battery compartment. The system further includes a second set of one or more switching devices that selectively connect a second power output of the battery compartment of the patient-connected medical device with a second power input of the electronic components based on a second polarity of the input voltage, wherein the first polarity is opposite the second polarity.

In accordance with one aspect, a method for electrically limiting leakage current in a patient-connected medical device is provided. The patient connected medical device includes a first set of one or more switching devices that selectively connects a first power output of a battery compartment of the patient-connected medical device with a first power input of electronic components of the patient-connected medical device based on a first polarity of input voltage from the battery compartment and a second set of one or more switching devices that selectively connects a second power output of the battery compartment with a second power input of the electronic components based on a second polarity of the input voltage. The second polarity is opposite the first polarity. Further, a patient of the patient connected medical device is electrically connected to the electronic components via one or more patient connections. The method includes inserting a battery into the battery compartment, such that the battery is electrically connected to a power output and one or more battery connection terminals of the battery compartment. The power output is one of the first power output and the second power output. The method further includes electrically connecting one of the battery connection terminals and the patient. The electrical connection is independent of the patient connections. Even more, the method includes obstructing current flow between the power output and a corresponding power input until the input voltage is total input voltage. The first set and/or the second set facilitate obstruction of the current flow.

In accordance with another aspect, a patient-connected medical device is provided. The patient-connected medical device includes a battery compartment for one or more batteries. The battery compartment connects the batteries in series and includes a first power output and a second power output. The system further includes electronic components including a first power input and a second power input. Even more, the system includes a first set of one or more switching devices that selectively connect the first power output with the first power input based on a first polarity of input voltage from the battery compartment. Moreover, the system includes a second set of one or more switching devices that selectively connect the second power output with the second power input based on a second polarity of the input voltage. The first polarity is opposite the second polarity.

One advantage resides in limiting leakage current on a patient.

Another advantage resides in adaptability to any number of batteries.

Another advantage resides in functionality when batteries are inserted in any order.

Another advantage resides in patient protection even if one or more batteries are not properly oriented.

Another advantage resides in amenability to inexpensive manufacturing techniques.

Another advantage resides in small size.

Another advantage resides in ease of use.

Another advantage resides in functionality with low impedance patient connections.

Another advantage resides in low power consumption.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
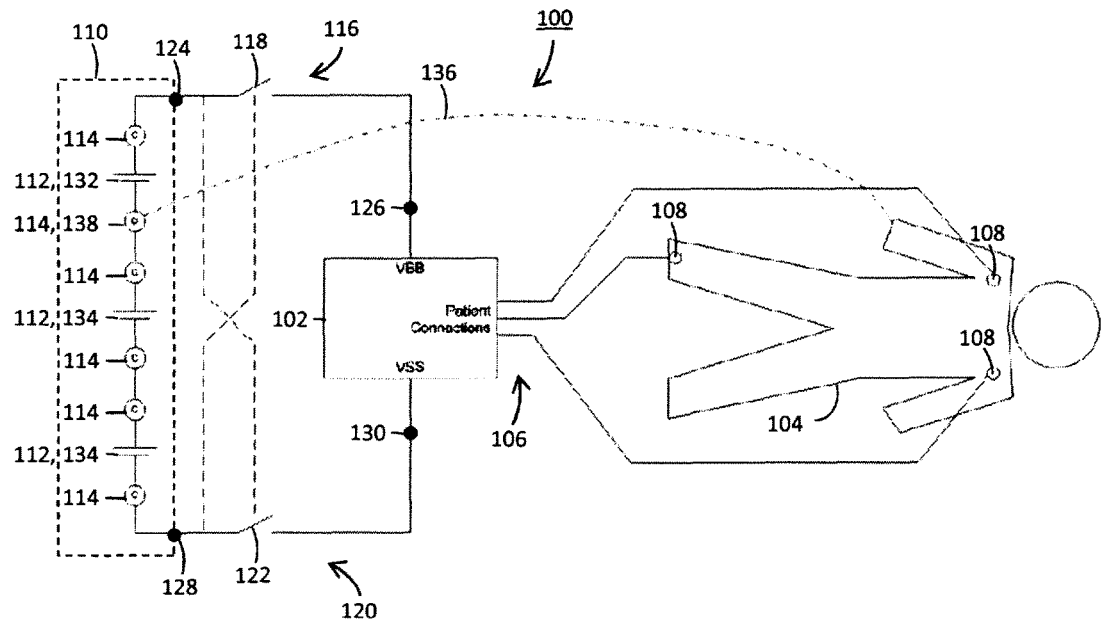
FIG. 1 is a conceptual view of a patient-connected medical device according to aspects of the present disclosure.

With reference to FIG. 1, a conceptual view of a patient-connected medical device 100 according to aspects of the present disclosure is provided. The patient-connected medical device 100 is suitably employed to monitor and/or provide life support functions. Further, the patient-connected medical device 100 is suitably mobile, worn on the patient's person. It is contemplated that, in certain embodiments, the patient-connected medical device 100 is one of a patient monitor, a pacemaker, and the like.

The patient-connected medical device 100 includes electronic components 102 connected to a patient 104 via one or more patient connections 106. It is contemplated that the patient connections 106 connect to the patient 104 via one or more of sensors and/or electrodes 108. In certain embodiments, the electronic components 102 receive patient data from the patient connections 106. Additionally or alternatively, in certain embodiments, the electronic components 102 provide signals to the patient connections 106. For example, if the patient 104 suffers from dysrhythmias, signals can be provided to one of the patient connections 106 to control an associated electrode of the sensors and/or electrodes 108, so as to shock the patient's heart and maintain a proper heart beat.

A battery compartment 110 of the patient-connected medical device 100 receives one or more batteries 112 and provides power from the batteries 112 to the electronic components 102 of the patient-connected medical device 100. Suitably, the battery compartment 110 includes one or more battery connection terminals 114 that interface with terminals of the batteries 112 and connect the batteries 112 in series. In certain embodiments, when the batteries 112 are inserted into the battery compartment 110, the battery connection terminals 114 are externally inaccessible. That is to say, one cannot access the battery connection terminals 114 of the batteries 112 from outside the battery compartment 110. While this is typically accomplished by with the physical design of the battery compartment 110, mechanical and/or electro-mechanical approaches to accomplishing this are also contemplated.

Disposed between the electronic components 102 and the battery compartment 110, the patient-connected medical device 100 includes a first set 116 of one or more switching devices 118 and a second set 120 of one or more switching devices 122. Each of the switching devices 118, 122 includes one or more electronic switches, such as field effect transistors (FETs), Triodes for Alternating Current (TRIACs), relays, and the like. Further, typically, the switching devices 118 of the first set 116 are connected in series and/or the switching devices 122 of the second set 120 are connected in series.

The first set 116 and the second set 120 are wired so current is inhibited from accidentally flowing from any of the battery connection terminals 114 to the patient 104, regardless of the order of installing the batteries 112 and/or the polarity (correct or incorrect) of the batteries 112. The first set 116 selectively connects, directly or indirectly, a first power output 124 of the battery compartment 110 to a first power input 126 of the electronic components 102, and the second set 120 selectively connects, directly or indirectly, a second power output 128 of the battery compartment 110 to a second power input 130 of the electronic components 102. By indirectly, it is contemplated that additional electronic components, such as resistors, are disposed between ones of the switching devices 118, 122 and one or more of the power inputs 126, 130, the power outputs 124, 128, and others of the switching devices 118, 122. Typically, the first power output 124 and the first power input 126 are positive and the second power output 128 and the second power input 130 are negative. However, in certain embodiments, the polarity of the batteries 112 can be reversed, whereby the first power output 124 and the first power input 126 can be negative and the second power output 128 and the second power input 130 can be positive.

The first set 116 and the second set 120 are electronically controlled by opposite polarity of total input voltage, so the sets 116, 120 do not connect their respective power inputs with their respective power outputs until all the batteries 112 are installed. That is to say, the first set 116 is electronically controlled by a first polarity of the total input voltage, and the second set 120 is electronically controlled by a second polarity, opposite the first polarity, of the total input voltage. The total input voltage is the voltage output by the battery compartment 110 (i.e., the voltage across the first power output 124 and the second power output 128) when completely filled with all the batteries 112. In certain embodiments, this control is implemented by controlling the first set 116 with the second power output 128 of the battery compartment 110 and the second set 120 with the first power output 124 of the battery compartment 110, as illustrated.

Without the switching devices 118, 122 and assuming fewer than all the batteries 112 are installed in the battery compartment 110, the patient 104 could come in contact with one of the battery connection terminals 114 and leakage current could result. For example, if a third one 132 of the batteries 112 was not installed, current could flow from the other ones 134 of the batteries 112 to the patient by way of a first path 136 and one of the patient connections 106. It is contemplated that the first path 136 could result from the patient 104 directly contacting one 138 of the battery connection terminals 114 of the third one 132 of the batteries 112 or indirectly by, for example, a caregiver simultaneously touching the one 138 of the battery connection terminals 114 and the patient 104.

Figure 2:
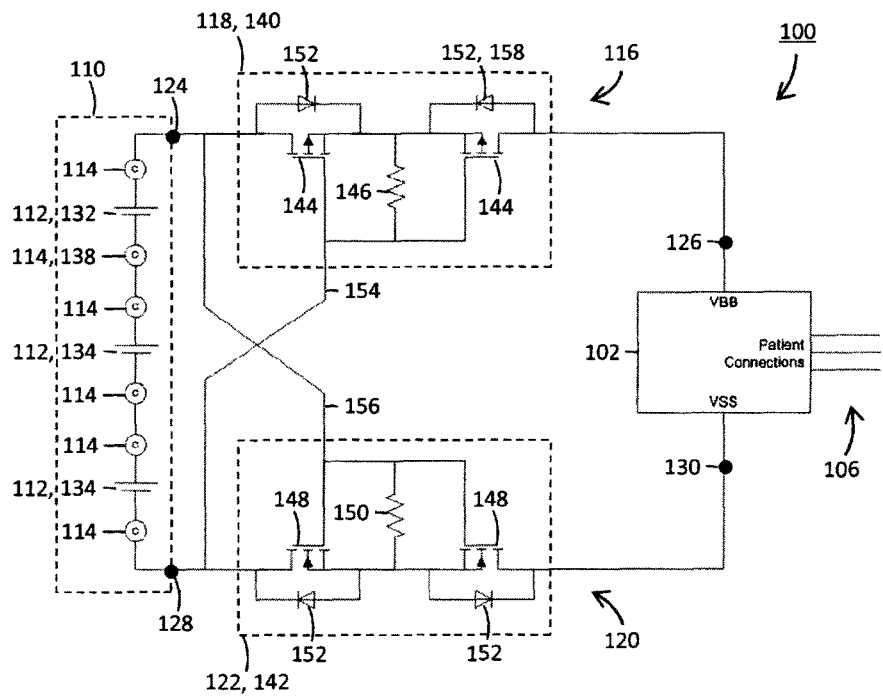
FIG. 2 is a detailed view of one embodiment of the patient-connected medical device of FIG. 1.

With reference to FIG. 2, a detailed embodiment of the patient-connected medical device 100 according to aspects of the present disclosure is provided. The first set 116 includes a first switching device 140, and the second set 120 includes a second switching device 142. The first switching device 140 includes two p-channel FETs 144 connected back-to-back and a resistor 146, and the second switching device 142 includes two n-channel FETs 148 connected back-to-back and a resistor 150. The FETs 144, 148 are connected back-to-back to prevent current from flowing in both directions through the switching devices 140, 142, because each of the FETs 144, 148 includes a substrate diode 152, which allows current to flow in one direction through the FET regardless of whether it is closed or open. The resistors 146, 150 are employed in conjunction with the substrate diodes 152 to bias the FETs 144, 148.

A control signal 154 from the second power output 128 of the battery compartment 110 electronically controls the p-channel FETs 144, and a control signal 156 from the first power output 124 of the battery compartment 110 electronically controls the n-channel FETs 148. In other words, the control signals 154, 156 for the switching devices 140, 142 are cross coupled to opposite polarities of the total input voltage. So long as the total input voltage when all the batteries 112 are installed in the battery compartment 110 is above the gate-to-source turn-on voltage of the FETs 144, 148, current can flow. Cross-coupling the control signals 154, 156 of the FETs 144, 148 isolates the control signals 154, 156 so that there can be no completed path through the patient 104 and back to the batteries 102.

One problem with employing FETs as provided in FIG. 2 is that there are unintended return paths. For example, if the third one 132 of the batteries 112 was not installed and the patient were to touch the one 138 of the battery connection terminals 114, current could flow out the first power input 126 through one 158 of the substrate diodes 152 and the resistor 146 of the first switching device 140 to the second power output 128. Accordingly, this embodiment is primarily used with a mechanical interlock or construction for blocking access to the battery connection terminals 114 or in devices that are not cardiac function (CF) rated. The solution is described hereafter in FIGS. 3 and 4. The potential unintended return path is a result of the substrate diodes 152, whereby it is to be appreciated that it is not necessarily applicable to other electronic switches.

While the switching devices 140, 142 disclosed in connection with FIG. 2 are tailored to FETs, it is to be appreciated that other electronic switches, such as relays and TRIACs, can be employed in lieu of FETs. Further, it is to be appreciated that when other electronic switches are employed, the circuits embodying the switching devices 140, 142 will vary from what is illustrated. For example, there is not necessarily a one-to-one mapping between other electronic switches and the FETs 144, 148. Each of the switching devices 140, 142 has a plurality of FETs because the substrate diodes 152 allow current flow in one direction. Other electronic switches, such as relays, may not suffer from such a limitation, whereby only a single electronic switch would be required.

Figure 3:
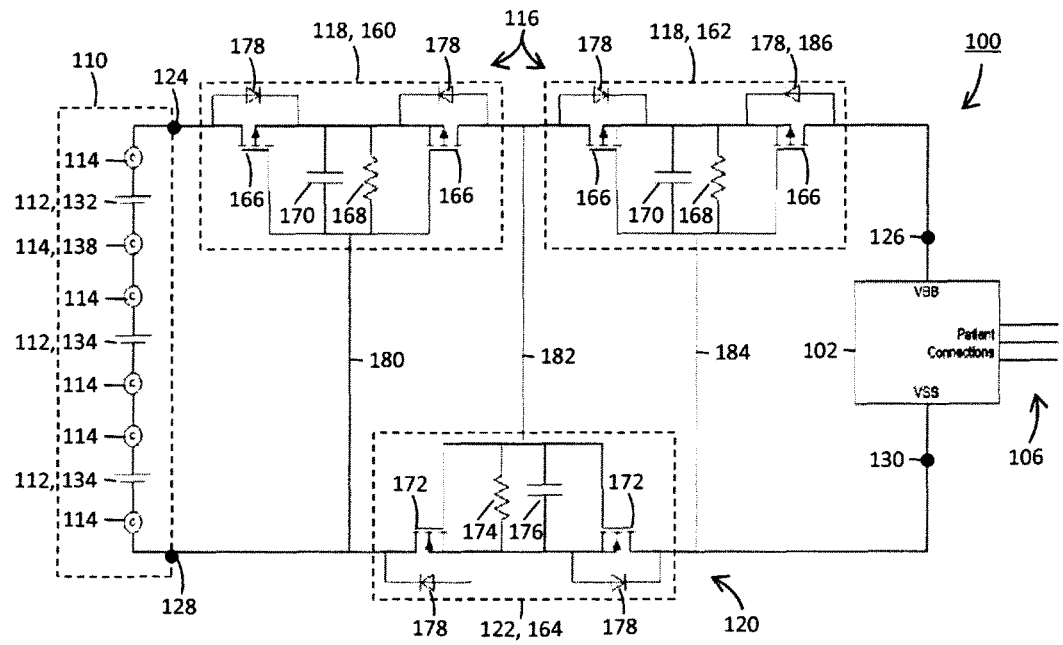
FIG. 3 is a detailed view of another embodiment of the patient-connected medical device of FIG. 1.

With reference to FIG. 3, another detailed embodiment of the patient-connected medical device 100 according to aspects of the present disclosure is provided. The first set 116 includes a first switching device 160 in series with a second switching device 162, and the second set 120 includes a third switching device 164. The first switching device 160 and the second switching device 162 each includes two p-channel FETs 166 connected back-to-back, a resistor 168, and an optional capacitor 170. Further, the third switching device 164 includes two n-channel FETs 172 connected back-to-back, a resistor 174, and an optional capacitor 176. The FETs 166, 172 are connected back-to-back to prevent current from flowing in both directions through the switching devices 160, 162, 164 because each of the FETs 166, 172 includes a substrate diode 178, which allows current to flow in one direction through the FET regardless of whether it is closed or open. The resistors 168, 174 are employed in conjunction with the substrate diodes 178 to bias the FETs 166, 172. The capacitors 170, 176 are optionally included to stabilize the switching behavior.

A control signal 180 from the second power output 128 of the battery compartment 110 electronically controls the p-channel FETs 166 of the first switching device 160, and a control signal 182 from the output or input (depending upon the flow of current) of the first switching device 160 electronically controls the n-channel FETs 172 of the third switching device 164. Further, a control signal 184 from the output or input (depending upon the flow of current) of the third switching device 164 electronically controls the p-channel FETs 166 of the second switching device 162. In other words, the first set 116 is electronically controlled by an opposite polarity of the total input voltage as the second set 120. So long as the total input voltage when all the batteries 112 are installed in the battery compartment 110 is above the gate-to-source turn-on voltage of the FETs 166, 172, current can flow.

As noted above, the embodiment of FIG. 2 suffers from unintended return paths when employing FETs because of the substrate diodes 152. The present embodiment prevents these unintended return paths by employing an additional switching device. For example, if the third one 132 of the batteries 112 was not installed and the patient were to touch the terminal 138 of the battery connection terminals 114, current could not flow out the first power input 126 through one 186 of the substrate diodes 178 and the resistor 168 of the second switching device 162 to the second power output 128 because of the third switching device 164.

While the switching devices 160, 162, 164 disclosed in connection with FIG. 3 are tailored to FETs, it is to be appreciated that other electronic switches, such as relays and TRIACs, can be employed in lieu of FETs. Further, it is to be appreciated that when other electronic switches are employed, the circuits embodying the switching devices 160, 162, 164 will vary from what is illustrated. For example, there is not necessarily a one-to-one mapping between other electronic switches and the FETs 166, 172. Each of the switching devices 160, 162, 164 required a plurality of FETs because the substrate diodes 178 allow current flow in one direction. Other electronic switches, such as relays, may not suffer from such a problem, whereby only a single electronic switch would be required.

Figure 4:
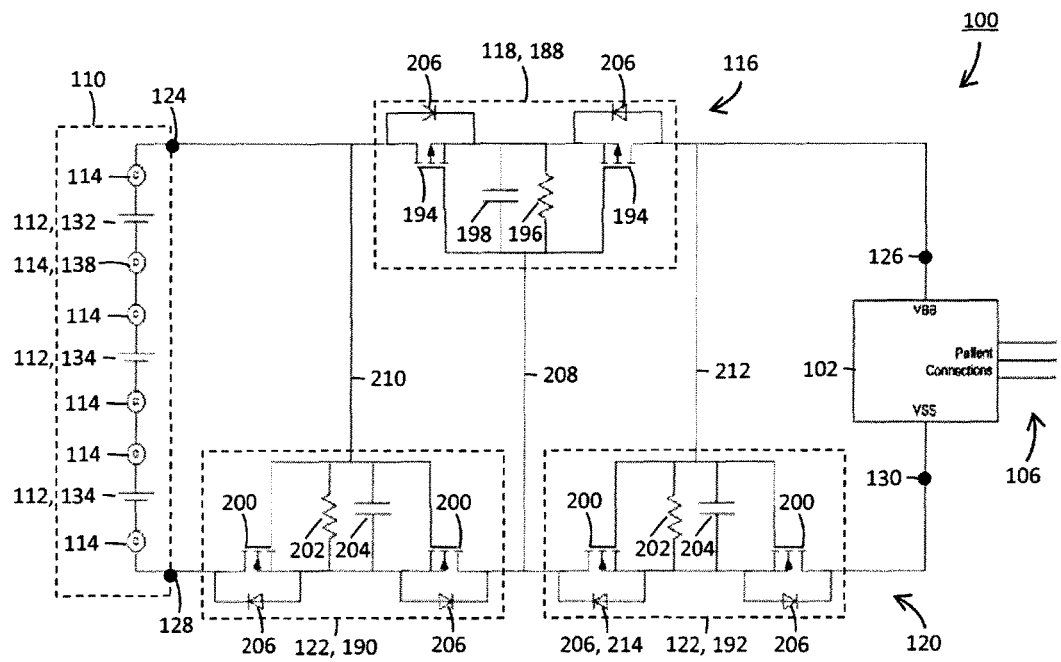
FIG. 4 is a detailed view of yet another embodiment of the patient-connected medical device of FIG. 1.

With reference to FIG. 4, yet another detailed embodiment of the patient-connected medical device 100 according to aspects of the present disclosure is provided. The first set 116 includes a first switching device 188, and the second set 120 includes a second switching device 190 in series with a third switching device 192. The first switching device 188 includes two p-channel FETs 194 connected back-to-back, a resistor 196, and an optional capacitor 198. Further, the second switching device 190 and the third switching device 192 each include two n-channel FETs 200 connected back-to-back, a resistor 202, and an optional capacitor 204. The FETs 194, 200 are connected back-to-back to prevent current from flowing in both directions through the switching devices 188, 190, 192 because each of the FETs 194, 200 includes a substrate diode 206, which allows current to flow in one direction through the FET regardless of whether it is closed or open. The resistors 196, 202 are employed in conjunction with the substrate diodes 206 to bias the FETs 194, 200. The capacitors 198, 204 are optionally included to stabilize the switching behavior.

A control signal 208 from the output or input (depending upon the flow of current) of the second switching device 190 electronically controls the p-channel FETs 194 of the first switching device 188. Further, a control signal 210 from the first power output 124 of the battery compartment 110 electronically controls the n-channel FETs 200 of the second switching device 190, and a control signal 212 from the output or input (depending upon the flow of current) of the first switching device 188 electronically controls the n-channel FETs 200 of the third switching device 192. In other words, the first set 116 is electronically controlled by an opposite polarity of the total input voltage as the second set 120. So long as the total input voltage when all the batteries 112 are installed in the battery compartment 110 is above the gate-to-source turn-on voltage of the FETs 194, 200, current can flow.

As noted above, the embodiment of FIG. 2 suffers from unintended return paths when employing FETs because of the substrate diodes 152. The present embodiment prevents these unintended return paths by employing an additional switching device. For example, if the third one 132 of the batteries 112 was not installed and the patient were to touch the one 138 of the battery connection terminals 114, current could not flow out the first power input 126 through the one 214 of the substrate diodes 206 of the third switching device 192 to the first power output 124 and/or the second power output 128 because of the first switching device 188 and/or the second switching device 190.

While the switching devices 188, 190, 192 disclosed in connection with FIG. 4 are tailored to FETs, it is to be appreciated that other electronic switches, such as relays and TRIACs, can be employed in lieu of FETs. Further, it is to be appreciated that when other electronic switches are employed, the circuits embodying the switching devices 188, 190, 192 will vary from what is illustrated. For example, there is not necessarily a one-to-one mapping between other electronic switches and the FETs 194, 200. Each of the switching devices 188, 190, 192 required a plurality of FETs because the substrate diodes 206 allow current flow in one direction. Other electronic switches, such as relays, may not suffer from such a problem, whereby only a single electronic switch would be required.

Figure 5:
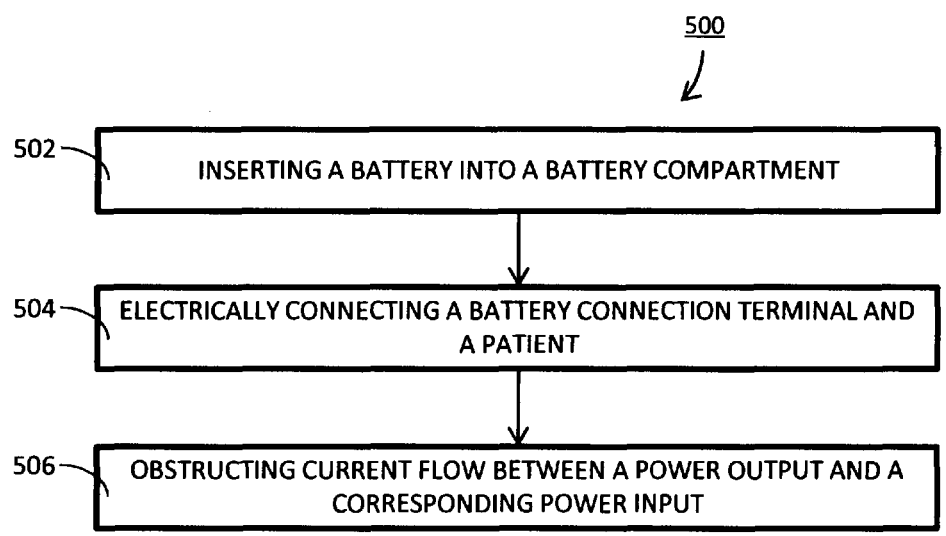
FIG. 5 illustrates a method of limiting leakage current according to aspects of the present disclosure.

With reference to FIG. 5, a method 500 for electrically limiting leakage current in the patient-connected medical device 100 is illustrated. A battery 112 is inserted 502 into the battery compartment 110 such that the battery 112 is electrically connected to a power output 124, 128 and one or more battery connection terminals 114 of the battery compartment 110. The power output 124, 128 is one of the first power output 124 and the second power output 128. Contemporaneous with or subsequent to the insertion 502, one of the battery connection terminals 114 is connected 504 with the patient 104, where the electrical connection is independent of the patient connections 106. For example, a nurse touches the battery connection terminal and the patient 104 while changing the batteries 114. As another example, the patient 104 accidently touches the battery connection terminal. Thereafter, current flow between the power output 124, 128 and a corresponding power input 126, 130 is obstructed 506 until the input voltage is total input voltage. Typically, the first set 116 and/or the second set 120 facilitate obstruction of the current flow by only closing associated switching devices when total input voltage is total input voltage. Further, the total input voltage is the voltage output by the battery compartment 110 when fully loaded with batteries.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A system for electrically limiting leakage current in a patient-connected medical device, comprising:
    a first set of one or more switching devices that selectively connect a first power output of a battery compartment of the patient-connected medical device with a first power input of electronic components of the patient-connected medical device controlled directly by a first polarity of input voltage from the battery compartment; and,
    a second set of one or more switching devices different from the first set of one or more switching devices that selectively connect a second power output of the battery compartment of the patient-connected medical device with a second power input of the electronic components controlled directly by a second polarity of the input voltage, wherein the first polarity is opposite the second polarity;
    wherein the first and second sets of one or more switching devices are disposed on opposing sides of the battery compartment.

2. The system according to claim 1, wherein the battery compartment is designed so battery connection terminals are inaccessible when all batteries of a specified type are installed in the battery compartment.

3. The system according to claim 1, wherein the first power output and/or the second power output are connected to the first power input and/or the second power input using one or more electronic switches.

4. The system according to claim 3, wherein the electronic switches include one or more of field effect transistors (FETs), Triodes for Alternating Current (TRIACs), and relays.

5. The system according to claim 1, wherein the first power output is connected with the first power input and/or the second power output is connected with the second power input, when the input voltage is total input voltage.

6. The system according to claim 5, wherein the total input voltage is a voltage output by the battery compartment when completely filled with batteries.

7. The system according to claim 1, wherein the first power output is indirectly connected with the first power input and/or the second power output is indirectly connected with the second power input.

8. The system according to claim 1, wherein the first power output and the first power input are positive and the second power output and the second power input are negative.

9. The system according to claim 1, wherein the first set selectively connects the first power output with the first power input based on the second power output, and the second set selectively connects the second power output with the second power input based on the first power output.

10. The system according to claim 1, wherein the first set includes a first switching device in series with a second switching device and the second set includes a third switching device, wherein the first switching device is controlled by the second power output, the second switching device is controlled by third switching device and/or the second power output, and the third switching device is controlled by the first switching device and/or the first power output.

11. The system according to claim 1, wherein the first set includes a first switching device and the second set includes a second switching device in series with a third switching device, wherein the first switching device is controlled by the second switching device and/or the third switching device, the second switching device is controlled by first power output and/or the first switching device, and the third switching device is controlled by the first switching device and/or the first power input.

12. A patient-connected medical device comprising:
   the battery compartment for one or more batteries, wherein the battery compartment connects the batteries in series and includes the first power output and the second power output;
   the electronic components including the first power input and the second power input; and,
   the system according to claim 1.

13. A method of manufacturing the system according to claim 1.

14. A method for electrically limiting leakage current in a patient-connected medical device with a system comprising, a first set of one or more switching devices that selectively connect a first power output of a battery compartment of the patient-connected medical device with a first power input of electronic components of the patient-connected medical device controlled directly by a first polarity of input voltage from the battery compartment; and a second set of one or more switching devices that selectively connect a second power output of the battery compartment of the patient-connected medical device with a second power input of the electronic components controlled directly by a second polarity of the input voltage, wherein the first polarity is opposite the second polarity; said method comprising:
   inserting a battery into the battery compartment, the battery electrically connected to a power output and one or more battery connection terminals of the battery compartment, wherein the power output is one of the first power output and the second power output;
   establishing an electrical conduction path between one of the battery connection terminals and the patient, wherein the electrical conduction path is independent of the patient connections;
   obstructing current flow between the power output and a corresponding power input until the input voltage is a preselected operating input voltage, wherein the first set and/or the second set of switching devices facilitate obstruction of the current flow;
   wherein the first and second sets of one or more switching devices are disposed on opposing sides of the battery compartment.

15. The method according to claim 14, wherein the obstructing includes:
   closing the switching devices of the first set when the input voltage of the first polarity is the total input voltage; and,
   closing the switching devices of the second set when the input voltage of the second polarity is the total input voltage.

16. The method according to claim 14, wherein the first set includes a first switching device in series with a second switching device and the second set includes a third switching device, wherein the first switching device is controlled by the second power output and/or the third switching device, the second switching device is controlled by third switching device and/or second power input, and the third switching device is controlled by the first switching device and/or the second switching device, wherein the obstructing includes:
   opening the first switching device until the input voltage of the first polarity is the preselected operating input voltage;
   opening the second switching device until the input voltage of the first polarity is the total input voltage and both the first switching device and the third switching device are closed; and,
   opening the third switching device until the input voltage of the second polarity is the total input voltage and the first switching device is closed.

17. The method according to claim 14, wherein the first set includes a first switching device and the second set includes a second switching device in series with a third switching device, wherein the first switching device is controlled by the second switching device and/or the third switching device, the second switching device is controlled by first power output and/or the first switching device, and the third switching device is controlled by the first switching device and/or the first power input;
   closing the first switching device when the input voltage of the first polarity is the total input voltage and second switching device is closed;
   closing the second switching device when the input voltage of the second polarity is the total input voltage; and,
   closing the third switching device when the input voltage of the second polarity is the total input voltage and both the first switching device and the second switching device are closed.

18. The method according to claim 14, wherein the preselected operating input voltage is a voltage output by the battery compartment when completely filled with batteries.

19. A patient-connected medical device, comprising:
   a battery compartment for one or more batteries, wherein the battery compartment connects the batteries in series and includes a first power output and a second power output;
   electronic components including a first power input and a second power input;
   a first set of one or more switching devices that selectively connect the first power output with the first power input controlled directly by a first polarity of input voltage from the battery compartment; and,
   a second set of one or more switching devices that selectively connect the second power output with the second power input controlled directly by a second polarity of the input voltage, wherein the first polarity is opposite the second polarity;
   wherein the first and second sets of one or more switching devices are disposed on opposing sides of the battery compartment.

20. The device according to claim 19, wherein the first set includes a first switching device in series with a second switching device and the second set includes a third switching device, wherein the first switching device is controlled by the second power output, the second switching device is controlled by third switching device and/or the second power output, and the third switching device is controlled by the first switching device and/or the first power output.

* * * * *